United States Patent
Noe et al.

(10) Patent No.: US 8,821,696 B2
(45) Date of Patent: Sep. 2, 2014

(54) METHODS AND EXTRACTION UNITS EMPLOYING VAPOR DRAW COMPOSITIONAL ANALYSIS

(71) Applicant: UOP LLC, Des Plaines, IL (US)

(72) Inventors: Jason L. Noe, Mount Prospect, IL (US); Ian Horn, Streamwood, IL (US); Lars Sullivan, Mount Prospect, IL (US); Bruce R. Beadle, Kildeer, IL (US); Edward M. Casey, Mount Prospect, IL (US); James W. Harris, Palatine, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 14/075,206

(22) Filed: Nov. 8, 2013

(65) Prior Publication Data

US 2014/0061021 A1   Mar. 6, 2014

Related U.S. Application Data

(62) Division of application No. 12/893,810, filed on Sep. 29, 2010, now Pat. No. 8,608,912.

(51) Int. Cl.
| | | |
|---|---|---|
| *B01D 3/40* | (2006.01) | |
| *B01D 3/42* | (2006.01) | |
| *C07C 7/08* | (2006.01) | |
| *G01N 25/14* | (2006.01) | |
| *B01D 11/04* | (2006.01) | |
| *G01N 21/35* | (2014.01) | |
| *G01N 1/22* | (2006.01) | |

(52) U.S. Cl.
CPC ............ *B01D 3/40* (2013.01); *B01D 11/0488* (2013.01); *B01D 11/043* (2013.01); *G01N 21/359* (2013.01); *G01N 2001/2282* (2013.01); *G01N 2021/3595* (2013.01); *G01N 1/2226* (2013.01)
USPC .......... 202/169; 202/260; 196/14.52; 422/531

(58) Field of Classification Search
CPC .............. B01D 3/40; B01D 3/42; C07C 7/08; G01N 25/14; G01N 25/142
USPC .............. 202/169, 254, 260, 270; 196/14.52; 422/531; 203/1, 3, 46, 58, DIG. 18; 208/313, 321, 326, DIG. 1; 73/23.35, 73/23.36
See application file for complete search history.

(56) References Cited

U.S. PATENT DOCUMENTS

| | | | | |
|---|---|---|---|---|
| 2,696,464 | A * | 12/1954 | Mathis et al. ................. | 202/160 |
| 3,445,347 | A * | 5/1969 | Borrel et al. ................... | 203/96 |
| 3,616,267 | A * | 10/1971 | McNeill et al. ................. | 203/3 |
| 3,985,624 | A * | 10/1976 | Prevost et al. ............. | 73/863.12 |
| 4,057,995 | A * | 11/1977 | Kleiss .......................... | 73/31.04 |
| 5,437,179 | A * | 8/1995 | Wiegand et al. ............. | 73/23.35 |
| 5,589,630 | A * | 12/1996 | Wiegand et al. ............. | 73/23.35 |
| 6,413,378 | B1* | 7/2002 | Kanauchi et al. ................ | 203/1 |
| 2007/0256920 | A1* | 11/2007 | Kanauchi et al. ................ | 203/2 |

* cited by examiner

*Primary Examiner* — Nina Bhat
*Assistant Examiner* — Jonathan Miller
(74) *Attorney, Agent, or Firm* — Mark R. Willis

(57) ABSTRACT

Embodiments of extraction unit and an analysis method are provided. In one embodiment, the analysis method includes the steps of providing a feed stream and a species-selective solvent to the distillation column, drawing a vapor sample from the distillation column, condensing the vapor sample, and analyzing at least a portion of the condensed vapor sample.

7 Claims, 3 Drawing Sheets

METHODS AND EXTRACTION UNITS EMPLOYING VAPOR DRAW COMPOSITIONAL ANALYSIS

CROSS REFERENCE TO RELATED APPLICATION

This application is a Division of prior copending application Ser. No. 12/893,810 which was filed Sep. 29, 2010, the contents of which are incorporated herein by reference thereto.

FIELD OF THE INVENTION

The present invention relates generally to extraction and, more particularly, to embodiments of an extraction unit and method employing a vapor draw to provide compositional analysis of material streams with reduced time lag.

DESCRIPTION OF RELATED ART

Extraction units are commonly utilized within various processing industries to separate feed streams into raffinate and extract streams for petrochemical, gasoline, and other applications. In the petro-chemical industry, specifically, extractive distillation and conventional extraction units are often utilized to separate hydrocarbon feed stocks into raffinate streams consisting primarily of non-aromatic hydrocarbons and extract streams consisting primarily of aromatic hydrocarbons, such as benzene, toluene, xylene, and other aromatic species. In one common extractive distillation process, a hydrocarbon feed stream is introduced into an intermediate section of an Extractive Distillation ("ED") column containing a series of stacked trays. A polar solvent, such as sulfolane, is continually circulated through the ED column, often in the presence of steam. The polar solvent contacts the feed stream within the ED column trays and predominately interacts with the hydrocarbon components having stronger polarities when interacting with the solvent to decrease the volatility of the aromatic extract relative to the non-aromatic raffinate. The non-aromatic raffinate is collected from the ED column via an overhead outlet while the extract, solvent, and water, if present, exits the ED column through a lower outlet as a rich solvent stream. The rich solvent stream is then directed into a second distillation column (commonly referred to as a "recovery column" or a "solvent recovery column") to separate the extract from the solvent and thereby provide a highly pure extract stream of the desired aromatic product. Commonly, in the conventional extraction process, the feed and solvent are first contacted in a liquid-liquid scheme and then are introduced as a single stream to the ED column (referred to as a "stripper" or "extractive distillation stripper" column)

On-line analyzers are commonly utilized within extraction units of the type described above to ensure satisfaction of purity standards. Certain extractive distillation and conventional extraction units also employ an on-line analyzer to provide analytical information regarding the composition of liquid samples taken from a location downstream of the ED column. The liquid sample is taken from a location downstream of the ED column (e.g., from the receiver of a recovery column) to minimize the liquid sample's solvent content, which, if undesirably high, can promote phase separation and dilute the liquid sample thus rendering detection of trace levels of contaminants more difficult. The on-line analyzer measures the presence of at least one component or contaminant within the liquid sample to determine sample purity. For example, the analyzer may measure the presence of non-aromatics or other contaminants in the extract aromatic stream. The analytical data provided by the analyzer may then be utilized to adjust one or more operational parameters of the extraction unit, if needed, to maintain extract purity within a desired range.

Conventional on-line analyzer systems of the type described above provide a relatively straightforward and accurate compositional analysis of liquid samples. However, due to the downstream location from which the liquid samples are taken, compositional changes taking place within the ED column due to, for example, process parameter adjustments are not fully detectable until well after such changes first occur and equilibrium is reached within the downstream equipment from which the liquid samples are taken. A significant time lag thus occurs between the current material conditions within the ED column and the analytical data provided by conventional on-line analyzer systems, which introduces undesirable uncertainties into process control.

There thus exists an ongoing demand to provide embodiments of an extraction unit and analysis method wherein analysis data is provided with a significant reduction in time lag as compared to conventional extraction units and analysis methods of the type described above. Other desirable features and characteristics of embodiments of the present invention will become apparent from the subsequent Detailed Description and the appended Claims, taken in conjunction with the accompanying Drawings and the foregoing Description of Related Art.

SUMMARY OF THE INVENTION

Embodiments of an analysis method are provided for use in conjunction with an extraction unit including a distillation column. In one embodiment, the analysis method includes the steps of providing a feed stream and a species-selective solvent to the distillation column, exposing a feed stream to a species-selective solvent, drawing a vapor sample from the distillation column, condensing the vapor sample, and analyzing at least a portion of the condensed vapor sample.

Embodiments of an extraction unit are further provided for separating a feed stream utilizing a species-selective solvent. In one embodiment, the extraction unit includes a distillation column that receives the feed stream and species-selective solvent, whether as a single stream or separate streams; a vapor draw fluidly coupled to the distillation column and configured to draw vapor samples therefrom during operation of the extraction unit; and an analyzer system fluidly coupled to the vapor draw and configured to measure the presence of at least one component within the vapor samples. In certain embodiments, the vapor sample may be separated into at least two liquid phases prior to analysis, and analysis is performed on at least one phase separated from the condensed vapor sample.

BRIEF DESCRIPTION OF THE DRAWINGS

Embodiments of the present invention will hereinafter be described in conjunction with the following drawing figures, wherein like numerals denote like elements, and wherein.

DETAILED DESCRIPTION

The following Detailed Description is merely exemplary in nature and is not intended to limit the invention or the application and uses of the invention. Furthermore, there is no intention to be bound by any theory presented in the preceding Description of Related Art or the following Detailed Description.

Various embodiments of the vapor draw analysis method and extraction unit contemplated herein provide analysis data with significant reduction in time lag as compared to conventional extraction units and analysis methods. In contrast to conventional analysis methods wherein liquid samples are taken from a location downstream of a distillation column (e.g., from a recovery column receiver), embodiments of the analysis method and extraction unit described below provide compositional profile data reflective of current or near current material conditions within a distillation column by drawing vapor samples directly therefrom. This results in a significant reduction in data time lag, which enables the extraction to be controlled in a more precise manner. Further, by employing a vapor draw to remove vapor samples from a distillation column, the amount of solvent present in a given vapor sample is greatly reduced, which minimizes dilution of the vapor sample and which reduces the likelihood of phase separation within the vapor sample. In certain embodiments, the amount of solvent in the analyzed portion of the vapor sample is still further reduced by separating the condensed vapor sample into at least two liquid phases, one of which contains little to no water or solvent, and analyzing the liquid phase containing little to no water or solvent, as further described below.

While primarily described below in the conjunction with an aromatic separation process, embodiments of the vapor draw analysis method contemplated herein can also be utilized in conjunction with other types of separation processes, including processes utilized to separate olefins from non-olefins and sulfur-containing species from non-sulfur-containing species. Furthermore, although described below in conjunction with a particular type of extractive distillation unit, embodiments of the vapor draw analysis method are by no means limited to usage in conjunction with a particular type of extractive distillation unit and may be performed in conjunction with various other types of extraction units, such as conventional extraction units. Embodiments of the vapor draw analysis method are also amenable to performance in conjunction with Udex and Carom separation processes commercially implemented by UOP, LLC (formerly "Universal Oil Products"), headquartered in Des Plaines, Ill.

Figure 1:
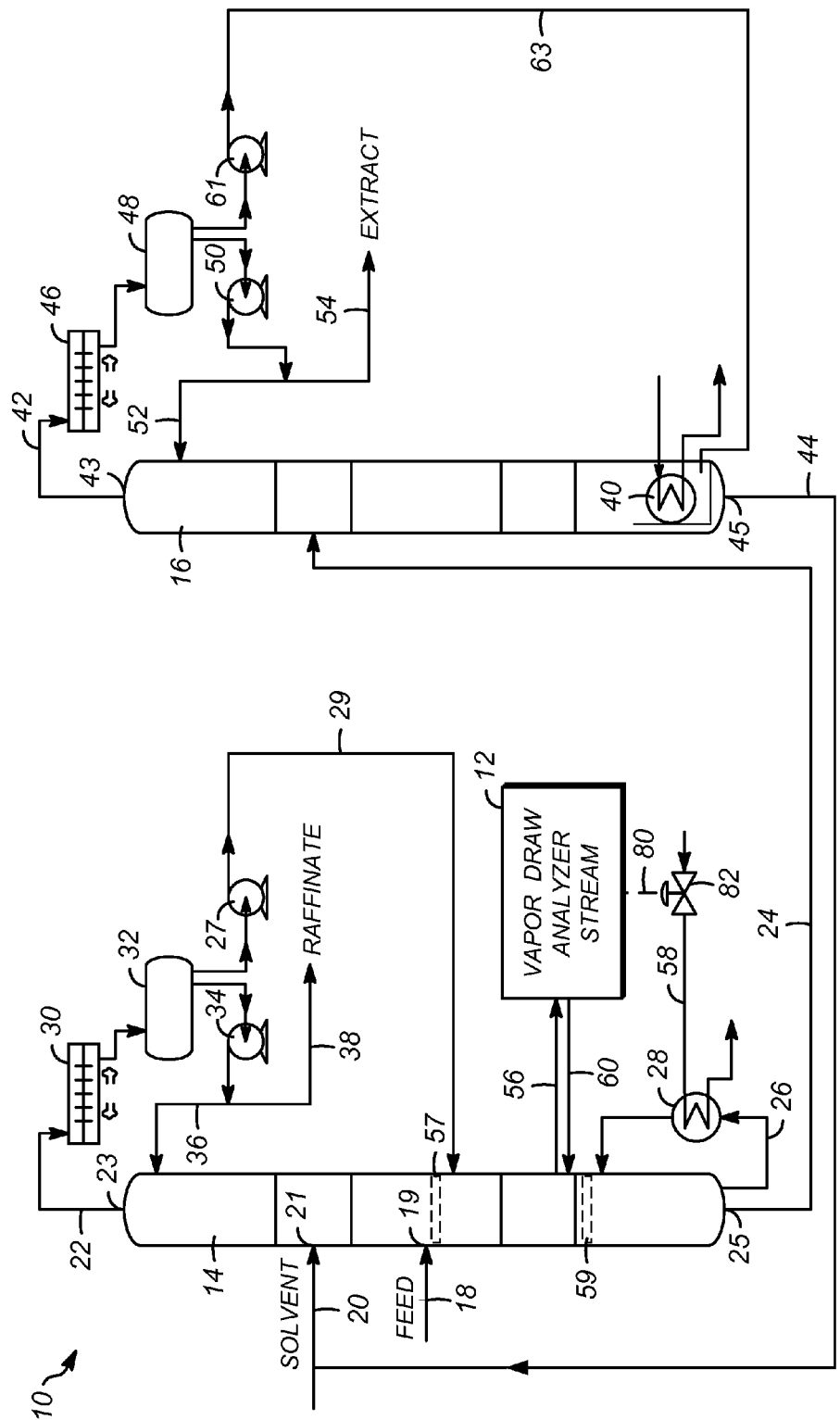
FIG. 1 is a schematic diagram of an extraction unit including a vapor draw analyzer system in accordance with an exemplary embodiment.

FIG. 1 is a schematic illustrating an extraction unit 10 including a vapor draw analyzer system 12 illustrated in accordance with an exemplary embodiment and suitable for performing embodiments of the vapor draw analysis method described below. In this particular example, extraction unit 10 assumes the form of an extractive distillation unit including two distillation columns, namely, an extractive distillation ("ED") column 14 and a recovery column 16 (also commonly referred to as a "solvent recovery column") The various components of extraction unit 10 are described in detail below to provide an exemplary context in which vapor draw analyzer system 12 and embodiments of the vapor draw method can be understood. Alternative embodiments of extraction unit 10 may, however, assume other forms (e.g., that of a conventional liquid-liquid extraction unit) and may include components other than those included in the exemplary embodiment described below.

With continued reference to FIG. 1, ED column 14 assumes the form of a vertically-oriented vessel containing a series of stacked trays; e.g., in one embodiment, ED column 14 contains between 50 and 90 real trays. During operation of extraction unit 10, a feed stream 18 is directed into a feed port 19 provided in, for example, an intermediate or middle section of ED column 14. In embodiments wherein extraction unit 10 is utilized to carry-out aromatic separation, feed stream 18 contains aromatic and non-aromatic hydrocarbon components. As appearing herein, the terms "aromatic," "aromatic hydrocarbon," and the like are utilized to denote a hydrocarbon containing one or more rings of unsaturated cyclic carbon radicals where one or more of the carbon radicals can be replaced by one or more non-carbon radicals. An exemplary aromatic compound is benzene having a $C_6$ ring containing three double bonds. Feed stream 18 may also contain other hydrocarbon molecules (e.g., straight-chain, branched, or cyclic alkanes, alkenes, alkadienes, alkynes, and alkenylbenzenes), various impurities (e.g., hydrogen, metals, sulfur, etc.), and/or water. In many cases, feed stream 18 will comprise a relatively wide boiling range mixture of benzene, toluene, and xylenes admixed with corresponding boiling range paraffins and naphthenes. The source from which feed stream 18 is derived will vary amongst applications. However, as a first example, feed stream 18 may be debutanized or depentanized effluent produced utilizing a conventional catalytic reforming unit. Alternatively, as a second example, feed stream 18 may be a liquid byproduct from a hydrocarbon cracking unit hydrotreated to saturate olefins and diolefins and to remove trace levels of sulfur and nitrogen contained therein.

During operation of extraction unit 10, a species-selective solvent stream 20 is introduced into ED column 14 via a solvent inlet port 21, which is conveniently positioned above the feed stream inlet. Aromatic-selective solvent stream 20 can contain any compound or class of compounds that interacts with the components of feed stream 18 to alter their relative volatility and thereby enable the separation thereof. In embodiments wherein extraction unit 10 is utilized in aromatic separation, solvent stream 20 will comprise an aromatic-selective solvent, which is at least partially polar and exhibits a greater affinity for the more aromatic hydrocarbons. More specifically, solvent stream 20 may contain a solvent compound including a five-member ring containing one atom of sulfur and four atoms of carbon with two oxygen atoms bonded to the sulfur atom of the ring. In a preferred embodiment, the solvent comprises 1,1-dioxide tetrahydrothiofuran or tetrahydrothiophene 1,1-dioxide (also known as "tetramethylene sulfone" and commonly referred to as "sulfolane"). A non-exhaustive list of additional exemplary solvent compounds that may be included in solvent stream 20 includes 2-sulfolene, 3-sulfolene, 2-methylsulfolane, 2-4-dimethyl sulfolane, methyl-2-sulfonylether, N-aryl-3-sulfonylamine, ethyl-3-sulfonyl sulfide, 2-sulfonylacetate, diethyleneglycol, polyethyleneglycol, dipropyleneglycol, polypropyleneglycol, dimethylsulfoxide, N-methylpyrrolidone, glycol-amine, glycols, and glycol ethers including polyethyleneglycolether, N-methyl-2-pyrrolidone, and N-formyl morpholine. The solvent-to-feed volume ratio may be about 1:1 to about 20:1 depending on operating conditions within ED column 14, the composition of feed stream 18, and other such factors.

As solvent stream 20 flows over the trays included within ED column 14, solvent stream 20 contacts feed stream 18.

Solvent stream 20 interacts primarily with the aromatic components included within feed stream 18 thereby reducing their volatility relative to the non-aromatic components included within stream 18. The components having the greatest volatilities after exposure to solvent stream 20 exit ED column 14 predominately via an overhead outlet 23 as light stream 22; while predominately the components having lower volatilities after exposure to solvent stream 20, along with the solvent, exit ED column 14 via a lower outlet 25 as a solvent rich stream 24 (also commonly referred to as a "lower stream" or a "bottoms stream"). In embodiments wherein ED column 14 is utilized in aromatic separation, light stream 22 will typically contain substantially all (e.g., conveniently at least 99 wt %, preferably at least 99.5 wt %, and more preferably at least 99.9 wt %) of the non-aromatic components introduced into ED column 14. Additionally, light stream 22 will often contain trace amounts of aromatics, solvent, and entrained water droplets, if water is introduced into ED column 14 during processing. By comparison, rich solvent stream 24 will typically contain substantially all (e.g., conveniently at least 90 wt %, preferably at least 95 wt %, and more preferably at least 99 wt %) of the aromatic hydrocarbons and aromatic-selective solvent. Rich solvent stream 24 may also include certain non-aromatic components, contaminants, and water.

Water is preferably, although not necessarily, directed into ED column 14 during operation of extraction unit 10 as a portion of the solvent stream 20 shown in FIG. 1. The steam condensing in the overhead system may also be collected and returned to ED column 14 (e.g., via a pump 27 and a water return conduit 29, as described below) to ensure that the net flow of water leaving column 14 is balanced by the majority of the water introduced into column through stream 20. Additionally vapor may be caused to rise through ED column 14 by a reboiler circuit, such as reboiler circuit 26 shown in FIG. 1. As will be described more fully below, the operational parameters of reboiler circuit 26, such as the heat duty of at least one reboiler 28 included within reboiler circuit 26, can be adjusted during the extraction process to control component separation and thereby maintain extract or raffinate purity within predetermined standards. By way of non-limiting example, the operating parameters of extraction unit 10 may be controlled to maintain the pressure within ED column 14 between approximately 12 kilopascal (kPa) and 380 kPa, the overhead temperature within column 14 within a range of approximately 50° C. and 70° C., and the bottoms temperature within column 14 within a range of approximately 70° C. and 260° C. during the extraction process. In embodiments wherein ED column 14 is utilized for aromatic separation and solvent stream 20 comprises sulfolane, reboiler circuit 26 is preferably controlled to maintain the bottoms temperature between approximately 150° C. and 200° C.

After exiting the overhead outlet of ED column 14, light stream 22 is received and condensed by a condenser 30, such as an air-cooled heat exchanger (illustrated) or a liquid-cooled heat exchanger, or both. Light stream 22 is then collected, in its condensate form, within a receiver 32, which is typically horizontally-oriented. A pump 34 is fluidly coupled to an outlet of receiver 32 and, when energized, circulates a portion of the condensed light stream back to an upper section of ED column 14 as a reflux stream 36. A portion of the condensed vapor is water which is preferably recycled to the ED column via the separate inlet nozzle located below feed stream inlet 19, as indicated in FIG. 1 at 29. The remainder of condensed light stream is withdrawn from extraction unit 10 as a raffinate stream 38. In embodiments wherein ED column 14 is utilized in aromatic separation, raffinate stream 38 will consist primarily of nonaromatic hydrocarbons, but may also contain a certain weight percentage of aromatic hydrocarbons. In particular, raffinate stream 38 conveniently includes up to 10 wt % aromatics, preferably contains less than 1 wt % aromatics, and more preferably contain less than 0.1 wt % aromatics. Raffinate stream 38 may also contain varying amounts of water depending upon the amount of water entrained in light stream 22 from which raffinate stream 38 is derived, whether light stream 22 is separated, and, if so, the conditions under which light stream 22 was separated. As previously indicated, a second pump 27 may also be fluidly coupled to a second outlet of condenser 30 to return water collected within condenser 30 to ED column 14, as shown in FIG. 1 at 29.

After leaving ED column 14, rich solvent stream 24 is directed into recovery column 16 to separate the extract component or components from the solvent. As was the case previously, steam may be introduced into recovery column 16 by, for example, a reboiler circuit 40 to promote component separation at lower temperatures and to help minimize degradation of the solvent. Recovery column 16 thus produces a second overhead or light stream 42, which is recovered through an overhead outlet 43; and a lean solvent stream 44, which is recovered through a lower outlet 45 and ultimately recycled back to ED column 14 with solvent stream 20 in the manner shown in FIG. 1. In embodiments wherein extraction unit 10 is utilized in aromatic separation, light stream 42 contains the desired aromatic product or products, such as benzene, toluene, and/or xylene. Lean solvent stream 44, by comparison, contains the solvent, water (if present), and relatively minor amounts of contaminants, such as aromatic hydrocarbons, non-aromatic hydrocarbons, and/or other components including organic compounds having a higher boiling point or a lower relative volatility than light stream 42.

After exiting recovery column 16, light stream 42 is condensed in much the same manner as is light stream 22 produced by ED column 14. That is, light stream 42 may be condensed by an overhead condenser 46, such as an air-cooled heat exchanger (illustrated) or a liquid-cooled heat exchanger, or both. A receiver 48 collects the condensed light stream from overhead condenser 46; and a pump 50, which is fluidly coupled to an outlet of receiver 48, draws the condensed light stream from receiver and returns a portion of the condensed light stream to an upper section of recovery column 16 as reflux 52. The remainder of the condensed light stream is withdrawn from extraction unit 10 as a final extract stream 54. In embodiments wherein ED column 14 is utilized in aromatic separation, extract stream 54 will contain the desired aromatic product and possibly water, which may be later separated from the aromatic product in a conventionally-known manner (e.g., utilizing a separate vessel having a water boot). A second pump 57 may also be fluidly coupled to a second outlet of receiver 48 to return water collected within receiver 48 to recovery column 16 proximate reboiler 40, as indicated in FIG. 1 at 59.

As noted above, and in contrast to conventional extraction units, extraction unit 10 further includes a vapor draw analyzer system 12. During operation of extraction unit 10, analyzer system 12 continually removes vapor samples from ED column 14 through a vapor draw (generically represented in FIG. 1 by line 56). By removing vapor samples from ED column 14 directly as opposed to a location downstream of column 14, analyzer system 12 is able to provide analytical data describing current or near current material conditions within ED column 14 with relatively little time lag. Furthermore, as the species-selective solvent within ED column 14 is primarily in a liquid phase, relatively little solvent will be present in a given vapor sample thereby avoiding the difficulties associated with high solvent contents (e.g., excessive phase separation and sample dilution). The amount of solvent in the analyzed portion of a given vapor sample may still further be reduced in certain embodiments by separating the vapor sample into at least two liquid phases, one of which contains little to no solvent, and analyzing the liquid phase containing the lesser solvent. The particular manner in which a given vapor sample may be processed and analyzed by vapor draw analyzer system 12 is described more fully below in conjunction with FIGS. 2 and 3.

Vapor draw 56 is preferably fluidly coupled to ED column 14 at approximately the location where the concentration of the component (or components) to be measured by analyzer system 12 is the highest. If, for example, it is desired to measure a quantity indicative of impurities within raffinate stream 38, the vapor draw may be fluidly coupled to ED column 14 between the feed stream inlet and the light stream overhead outlet, such as a few trays below the lean solvent inlet. Conversely, if it is desired to measure a quantity indicative of impurities within rich solvent stream 24, vapor draw 56 may be fluidly coupled to ED column 14 between the feed stream inlet and the lower outlet through which rich solvent stream 24 flows, as generally shown in FIG. 1. In this latter case, vapor draw 56 is preferably fluidly coupled to ED column 14 between the feed tray and the bottommost tray (generically represented in FIG. 1 by dashed boxes 57 and 59, respectively) and, more preferably, fluidly coupled to ED column 14 within the range of the bottom ten trays. In embodiments wherein extraction unit 10 is utilized in aromatic separation, vapor draw 56 is preferably positioned at a location sufficient to ensure that the total non-aromatic components included within the vapor sample (or, more generally stated, "impurities of interest") does not exceed about 1 wt % and, more preferably, that the total non-aromatics within the vapor sample is less than about 0.5 wt %.

In a preferred embodiment, the analytical data generated by analyzer system 12 is utilized to adjust at least one operation parameter of extraction unit 10, such as the heat output of reboiler 28. Adjustments to the operational parameters of extraction unit 10 based upon analytical data generated by analyzer system 12 may be carried-out pursuant to either an open loop or a closed loop control scheme. For example, the data generated by analyzer system 12 may be utilized to determine appropriate parameter adjustments that are manually implemented. Alternatively, analyzer system 12 may be configured to automatically adjust at least one operational parameter of extraction unit 10 as a function of the measured quantities of a component (or components) of interest. More specifically, and as indicated in FIG. 1 by dashed line 58, analyzer system 12 may be operably coupled to reboiler 28 and configured to automatically adjust the heat duty of reboiler 28 as a function of the analytical data generated by analyzer system 12. Additional operational parameters of extraction unit 10 that may be adjusted in response to generated analytical data include, but are not limited to, ED column reflux, ED column pressure, solvent stream inlet temperature, feed stream inlet temperature, and the like. After sample analysis, the condensed vapor sample may be returned to ED column 14 via a return conduit 60 or, instead, simply purged.

Figure 2:
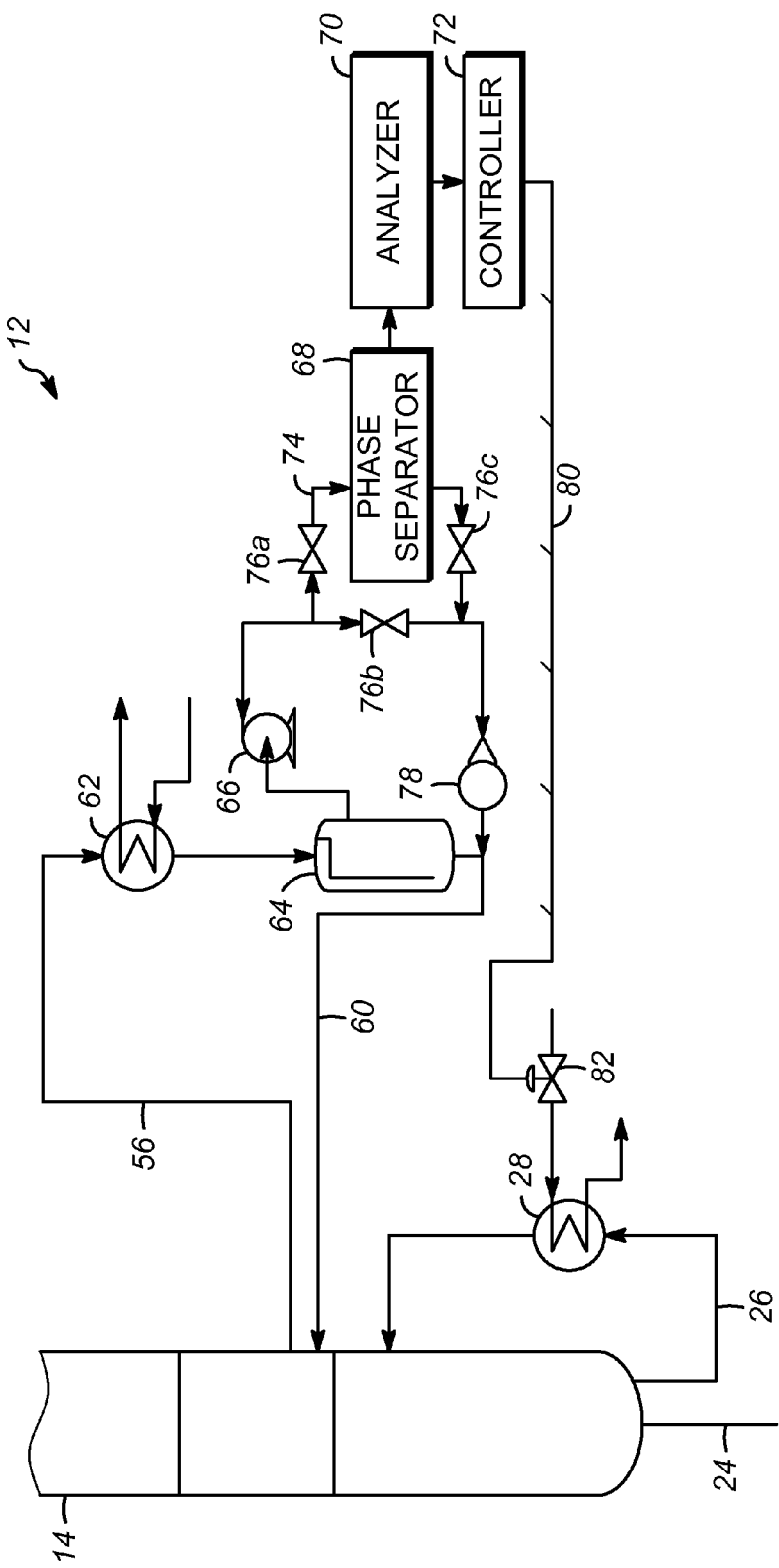
FIG. 2 is a schematic diagram illustrating an exemplary vapor draw analyzer system suitable for use as the analyzer system shown in FIG. 1.

FIG. 2 is a schematic diagram illustrating vapor draw analyzer system 12 in greater detail in accordance with one exemplary implementation. In this particular example, analyzer system 12 includes a condenser 62, which is fluidly coupled to an outlet of vapor draw 56; a vertical tank or receiver/phase separator 64, which is fluidly coupled to an outlet of condenser 62; a pump 66, which is fluidly coupled to an outlet of receiver/phase separator 64; at least one analyzer 70, which is fluidly coupled to an outlet of pump 66; and at least one controller 72, which is operably coupled to an output of analyzer 70. In embodiments wherein vapor draw analyzer system 12 is configured to automatically adjust the heat duty of reboiler 28, an output of controller 72 may also be operably coupled to a reboiler control valve 82 regulating the flow of heated water to reboiler 28, as indicated in FIG. 2 by control line 80. Analyzer 70 may be fluidly coupled to pump 66 by way of a flow loop 74 including a bypass flow loop through valve 76. During operation of analyzer system 12, flow control valve 76 can be adjusted, as appropriate, to control the flow rate to analyzer 70 to ensure that the capacity of analyzer 70 is not exceeded regardless the flow output of pump 66. As further indicated in FIG. 2 at 60, an outlet of receiver/phase separator 64 and an outlet of analyzer 70 may each be fluidly coupled to a sample return inlet fluidly coupled to ED column 14 at, for example, a location immediately below vapor draw 56. If desired, a flow indicator 78 may be positioned downstream of flow control loop 74 to monitor the flow rate of the vapor samples returned to ED column 14.

Many of the components included within vapor draw analyzer system 12 are conventionally known and will consequently not be described in greater detail other than to note the following. Condenser 62 may comprise any device or assemblage of devices suitable for condensing a substantial portion of the vapor samples received through vapor draw 56 by reducing vapor sample temperature or increasing vapor sample pressure. In the illustrated exemplary embodiment, specifically, condenser 62 assumes the form of a liquid-cooled (e.g., water-cooled) heat exchanger. Receiver/phase separator 64 may comprise any device or devices suitable for separating a condensed vapor samples into at least two liquid phases. In a preferred embodiment, receiver/phase separator 64 assumes the form of or includes either a decanter-type phase separator or a cyclone-type separator (also commonly referred to as a "centrifugal separator"). Analyzer 70 may comprise any instrument or instruments suitable for measuring, either directly or indirectly, the presence of at least one component or contaminant in a selected liquid phase of the condensed vapor sample. For example, analyzer 70 may comprise one or more gas chromatograph, near-infrared spectroscopic, and Fourier transform infrared spectroscopic instruments. In a preferred embodiment wherein analyzer 70 is utilized to detect non-aromatic components in an aromatic extract stream or aromatic components in a non-aromatic raffinate stream, analyzer 70 comprises a gas chromatograph. Analyzer 70 may also include a non-illustrated controller. Finally, controller 72 may comprise, or be associated with, any suitable number of individual microprocessors, memories, power supplies, storage devices, interface cards, and other standard components known in the art. Controller 72 may also include or cooperate with any number of software programs or instructions designed to carry-out the various methods, process tasks, calculations, and control functions set-forth herein.

Figure 3:
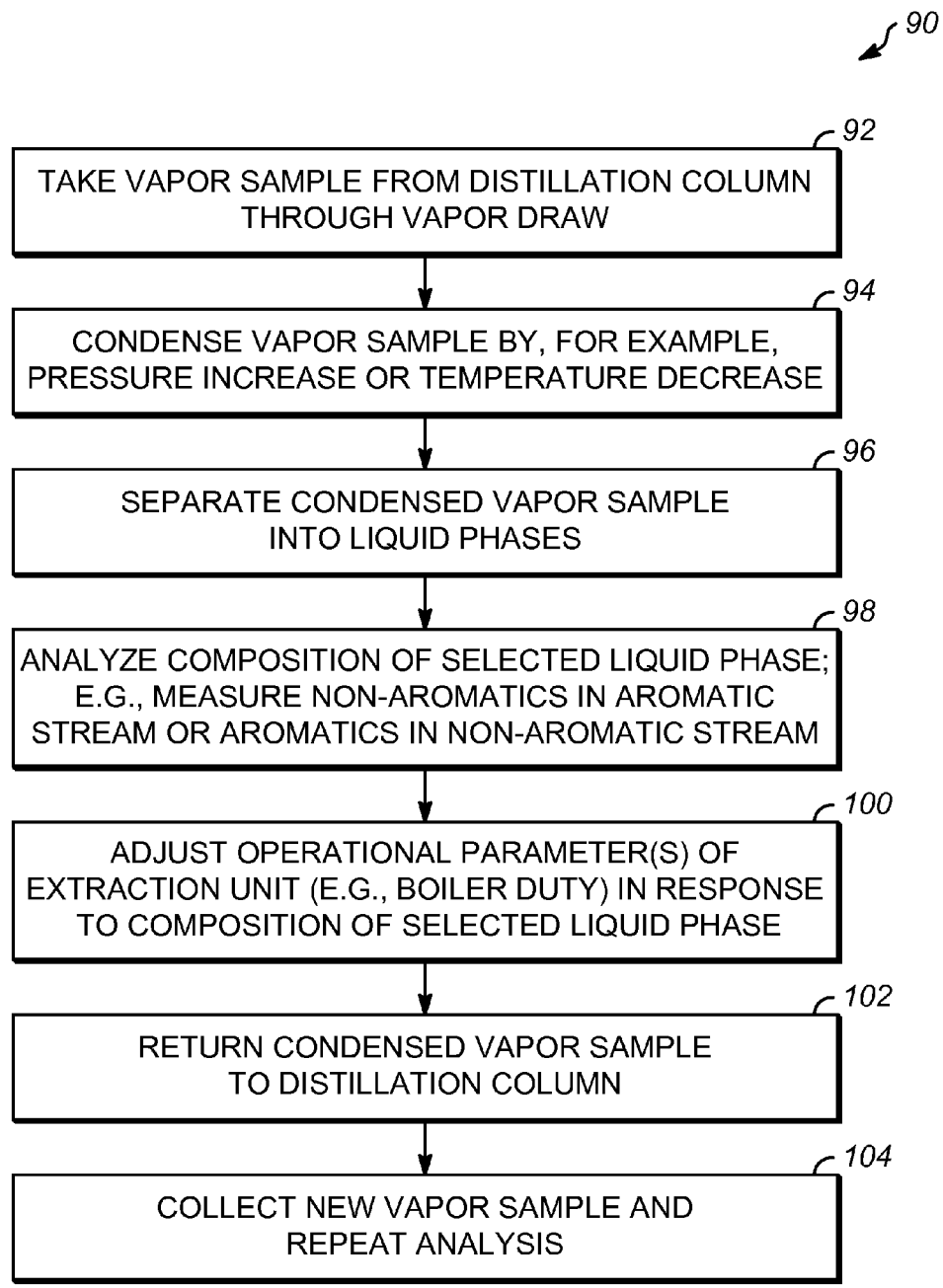
FIG. 3 is a flowchart illustrating an exemplary vapor draw analysis method that can be carried-out by the vapor draw analyzer system shown in FIG. 2.

FIG. 3 is a flowchart illustrating an exemplary vapor draw analysis method 90 that may be carried-out by exemplary vapor draw analyzer system 12. Referring collectively to FIGS. 2 and 3, analysis method 90 commences with the removal of at least one vapor sample from ED column 14 through vapor draw 56 (STEP 92, FIG. 3). Next, at STEP 94 (FIG. 3), the vapor sample is condensed within condenser 62. Receiver/phase separator 64 then receives the condensed vapor sample from condenser 62 and separates the sample into at least two liquid phases (STEP 96, FIG. 3). A selected phase (or phases) of the condensed vapor sample is subsequently drawn from receiver/phase separator 64 by pump 66 and supplied to analyzer 70 for compositional analysis (STEP 98, FIG. 3). In particular, during STEP 98, analyzer 70 may measure the selected liquid phase to determine the quantity of at least one component of interest, such as the quantity of one or more components indicative of raffinate impurities in an extract stream or indicative of extract impurities in a raffinate stream. The analytical data generated by analyzer 70 during STEP 98 is provided to controller 72, which then determines if adjustments to the operational parameters of extraction unit 10 are required to maintain the extract or raffinate streams within predetermined purity standards. If determining that operational adjustments are required, controller 72 implements these adjustments (STEP 100, FIG. 3). For example, if determining that the heat duty of reboiler 28 should be increased or decreased, controller may command 80 reboiler control valve 82 to a more open or closed position. Finally, at STEP 102 (FIG. 3), the condensed vapor sample is returned to ED column 14 through vapor sample return conduit 60. After returning the condensed vapor sample to ED column 14, analyzer system 12 may collect a new sample and repeat vapor draw analysis method 90, as indicated in FIGS. 3 at 104 and 106, to provide continual and rapid compositional analysis of the material stream of interest.

The foregoing has thus provided exemplary embodiments of analysis method and extraction unit wherein compositional profile data is obtained in a highly efficient manner and, in certain embodiments, utilized to adjust one or more operational parameters of the extraction unit. In contrast to conventional analysis methods wherein liquid samples are taken from a location downstream of a distillation column (e.g., from a recovery column receiver), the above-described analysis method provides compositional profile data reflective of current or near current material conditions within a distillation column (e.g., ED column 14) by drawing vapor samples directly therefrom. This results in a significant reduction in data time lag, which enables the extraction to be controlled in a more precise manner. Further, by employing a vapor draw to remove vapor samples from a distillation column, the amount of solvent present in a given vapor sample is greatly reduced, which minimizes dilution of the vapor sample and which reduces the likelihood of phase separation within the vapor sample. In certain embodiments, the amount of solvent in the analyzed portion of the vapor sample is still further reduced by separating the condensed vapor sample into at least two liquid phases, one of which contains little to no solvent, and analyzing the liquid phase containing little to no solvent as previously described.

While the exemplary analysis method was described above in conjunction with a particular type of extractive distillation unit, embodiments of the analysis method are equally applicable to other types of extraction units, including conventional liquid-liquid extraction units. Notably, in the case of a liquid-liquid extraction unit, the feed stream and species-selective solvent are contacted upstream of the distillation column and then subsequently provided to or received by the distillation column as a single stream. Thus, in both extraction distillation and liquid-liquid extraction techniques, a feed stream and a species-selective solvent are provided to a distillation column as either a single stream (in the case of liquid-liquid extraction) or as separate streams (in the case of extractive distillation). The location of the vapor draw will, of course, vary depending upon extraction unit type and the particular component or components measured during analysis. For example, in the case of a conventional extraction unit including a stripper column, the vapor draw is conveniently taken from the stripper column's bottom section. While primarily described above in the exemplary context of aromatic separation, embodiments of the vapor draw analysis method and vapor draw analysis system are by no means limited usage in conjunction with aromatic separation processes and can also be utilized in conjunction with processes utilized to separate olefins from non-olefins and sulfur-containing species from non-sulfur-containing species.

While at least one exemplary embodiment has been presented in the foregoing Detailed Description, it should be appreciated that a vast number of variations exist. It should also be appreciated that the exemplary embodiment or exemplary embodiments are only examples, and are not intended to limit the scope, applicability, or configuration of the invention in any way. Rather, the foregoing Detailed Description will provide those skilled in the art with a convenient road map for implementing an exemplary embodiment of the invention, it being understood that various changes may be made in the function and arrangement of elements described in an exemplary embodiment without departing from the scope of the invention as set forth in the appended Claims and their legal equivalents.

What is claimed is:

1. An extraction unit for separating a feed stream utilizing a species-selective solvent, the extraction unit comprising:
    a distillation column configured to receive the feed stream and the species-selective solvent;
    a vapor draw fluidly coupled to the distillation column and configured to draw vapor samples therefrom;
    a condenser configured to condense the vapor samples from the vapor draw to form condensed vapor samples;
    a separator configured to separate each of the condensed vapor samples into a first liquid phase and a second liquid phase; and
    an analyzer system fluidly coupled to the separator and comprising an analyzer configured to measure the presence of at least one component within the first liquid phase, the second liquid phase or both.

2. An extraction unit according to claim 1 wherein the analyzer is selected from the group consisting of a gas chromatograph, a near-infrared spectroscopic instrument, and a Fourier transform infrared spectroscopic instruments.

3. An extraction unit according to claim 1 wherein the analyzer system further comprises a controller operably coupled to the analyzer and configured to adjust at least one operational parameter of the extraction unit in response to analytical data generated by the analyzer.

4. An extraction unit according to claim 3 further comprising a reboiler fluidly coupled to the distillation column, the controller operably coupled to the reboiler and configured to adjust the heat duty thereof in response to analytical data generated by the analyzer.

5. An extraction unit according to claim 1 further comprising a vapor sample return conduit fluidly coupling the analyzer system to the distillation column.

6. An extraction unit according to claim 1 further comprising a feed tray disposed within the distillation column, the vapor draw fluidly coupled to distillation column below the feed tray.

7. An extraction unit according to claim 6 wherein the distillation column includes a lower outlet through which a rich solvent stream flows, and wherein the analyzer is configured to measure at least one quantity within the vapor sample indicative of raffinate impurities within the rich solvent stream.

* * * * *